US012797549B2

(12) United States Patent
Pala

(10) Patent No.: US 12,797,549 B2
(45) Date of Patent: Nov. 17, 2026

(54) DRUG DELIVERY DEVICE WITH ADHESIVE ASSEMBLY

(71) Applicant: Becton, Dickinson and Company, Franklin Lakes, NJ (US)

(72) Inventor: Trivikrama Bhanoji Pala, Parsippany, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 805 days.

(21) Appl. No.: 18/037,345

(22) PCT Filed: Nov. 18, 2021

(86) PCT No.: PCT/US2021/059808
§ 371 (c)(1),
(2) Date: May 17, 2023

(87) PCT Pub. No.: WO2022/109082
PCT Pub. Date: May 27, 2022

(65) Prior Publication Data

US 2023/0414877 A1 Dec. 28, 2023

Related U.S. Application Data

(60) Provisional application No. 63/116,030, filed on Nov. 19, 2020.

(51) Int. Cl.
*A61M 5/24* (2006.01)

(52) U.S. Cl.
CPC ........... *A61M 5/24* (2013.01); *A61M 2205/02* (2013.01)

(58) Field of Classification Search
CPC ...... A61M 5/24; A61M 5/1454; A61M 5/162; A61M 5/2466; A61M 5/14244;
(Continued)

(56) References Cited

U.S. PATENT DOCUMENTS

| | | | | |
|---|---|---|---|---|
| 6,843,782 | B2 | 1/2005 | Gross et al. | |
| 7,250,037 | B2 * | 7/2007 | Shermer | A61M 5/14248 604/134 |

(Continued)

FOREIGN PATENT DOCUMENTS

| | | | |
|---|---|---|---|
| CN | 1671430 | A | 9/2005 |
| CN | 105107064 | A | 12/2015 |

(Continued)

*Primary Examiner* — Laura A Bouchelle
*Assistant Examiner* — Sarah Dympna Grasmeder
(74) *Attorney, Agent, or Firm* — The Webb Law Firm

(57) ABSTRACT

A drug delivery device includes a housing, a container received within the housing, a drive assembly configured to move a stopper within the container, a needle having a retracted position and, a needle shield secured to the housing and receiving a portion of the needle, and an adhesive assembly including an adhesive layer secured to the bottom surface of the housing and a liner secured to the adhesive layer. The liner is configured to be removed from the adhesive layer and includes one of a protrusion and a liner opening, with the needle shield including the other of the protrusion and the liner opening. The protrusion is received by the liner opening to secure the liner to the needle shield, with the liner configured to be separated from the adhesive layer upon removal of the needle shield from the housing.

10 Claims, 11 Drawing Sheets

(58) Field of Classification Search
CPC ........ A61M 2205/02; A61M 2205/583; A61M 2205/585; A61M 2005/14256; A61M 2005/2414; A61M 2005/247
See application file for complete search history.

(56) References Cited

U.S. PATENT DOCUMENTS

| | | | |
|---|---|---|---|
| 8,961,469 | B2 | 2/2015 | Sonderegger et al. |
| 9,427,529 | B2 | 8/2016 | Cabiri |
| 10,391,245 | B2 | 8/2019 | Cronenberg et al. |
| 10,434,250 | B2 | 10/2019 | Sonderegger et al. |
| 2012/0316506 | A1 | 12/2012 | Sonderegger et al. |
| 2013/0155153 | A1 | 6/2013 | Duby et al. |
| 2013/0165866 | A1 | 6/2013 | Christensen |
| 2014/0171881 | A1 | 6/2014 | Cabiri |
| 2014/0179774 | A1 | 6/2014 | Chang et al. |
| 2016/0058941 | A1 | 3/2016 | Wu et al. |
| 2016/0367752 | A1 | 12/2016 | Cindrich et al. |
| 2017/0100542 | A1 | 4/2017 | Norton et al. |
| 2019/0083702 | A1 | 3/2019 | Nekouzadeh et al. |
| 2019/0117133 | A1* | 4/2019 | Halac .................. A61B 5/1473 |
| 2019/0120784 | A1 | 4/2019 | Halac et al. |
| 2019/0381239 | A1* | 12/2019 | Cabiri .............. A61M 5/14248 |

FOREIGN PATENT DOCUMENTS

| | | | |
|---|---|---|---|
| CN | 109310816 | A | 2/2019 |
| CN | 109789268 | A | 5/2019 |
| CN | 111770768 | A | 10/2020 |
| JP | 2018531134 | A | 10/2018 |
| WO | 2012134588 | A1 | 10/2012 |
| WO | 2015048791 | A1 | 4/2015 |
| WO | 2015081337 | A2 | 6/2015 |

* cited by examiner

DRUG DELIVERY DEVICE WITH ADHESIVE ASSEMBLY

CROSS-REFERENCE TO RELATED APPLICATIONS

This application is the United States national phase of International Application No. PCT/US2021/059808 filed Nov. 18, 2021, and claims priority to United States Provisional Application Ser. No. 63/116,030, filed Nov. 19, 2020, entitled "Drug Delivery Device with Adhesive Assembly", the entire disclosures of which are hereby incorporated by reference in their entirety.

BACKGROUND OF THE INVENTION

Field of the Invention

The present disclosure relates generally to a drug delivery device and, in particular, to a drug delivery device with an adhesive liner.

Description of Related Art

Various types of automatic injection or drug delivery devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

SUMMARY OF THE INVENTION

In one aspect, a drug delivery device includes a housing having a top surface and a bottom surface, a container received within the housing, the container configured to receive a medicament, with the container comprising a stopper configured to move within the container, a drive assembly configured to move the stopper, a needle having a retracted position where the needle is positioned within the housing and an extended position where a portion of the needle protrudes from the housing, a needle shield secured to the housing and receiving a portion of the needle, and an adhesive assembly comprising an adhesive layer secured to the bottom surface of the housing and a liner secured to the adhesive layer. The liner is configured to be removed from the adhesive layer. The liner includes one of a protrusion and a liner opening and the needle shield includes the other of the protrusion and the liner opening. The protrusion is received by the liner opening to secure the liner to the needle shield. The liner is configured to be separated from the adhesive layer upon removal of the needle shield from the housing.

The liner may include the protrusion and the needle shield may include the liner opening. The liner and the adhesive layer may define a clearance opening that receives a portion of the protrusion.

The liner may include a main body covering at least a portion of the adhesive layer and an extension portion extending from the main body, with the extension portion of the liner including one of the protrusion and the liner opening. The needle shield may be positioned between the main body of the liner and the extension portion of the liner. The main body of the liner may entirely cover the adhesive layer. The protrusion and the liner opening may form a snap-fit.

In a further aspect, an adhesive assembly for a drug delivery device including a housing, a needle having a retracted position where the needle is positioned within the housing and an extended position where a portion of the needle protrudes from the housing, and a needle shield secured to the housing and receiving a portion of the needle, includes: an adhesive layer configured to be secured to a bottom surface of the housing; and a liner secured to the adhesive layer, with the liner is configured to be removed from the adhesive layer. The liner includes a protrusion configured to be received by a liner opening defined by the needle shield, where the liner is configured to be separated from the adhesive layer upon removal of the needle shield from the housing.

The liner and the adhesive pad may define a clearance opening that receives a portion of the protrusion. The liner may include a main body covering at least a portion of the adhesive layer and an extension portion extending from the main body, with the protrusion positioned on the extension portion of the liner. The liner may include a folding line separating the main body of the liner from the extension portion of the liner, with the extension portion of the liner configured to be folded relative to the main body of the liner about the folding line. The main body of the liner may entirely cover the adhesive layer. The protrusion of the liner is configured to be snap-fit to the needle shield.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

DETAILED DESCRIPTION

Figure 1:
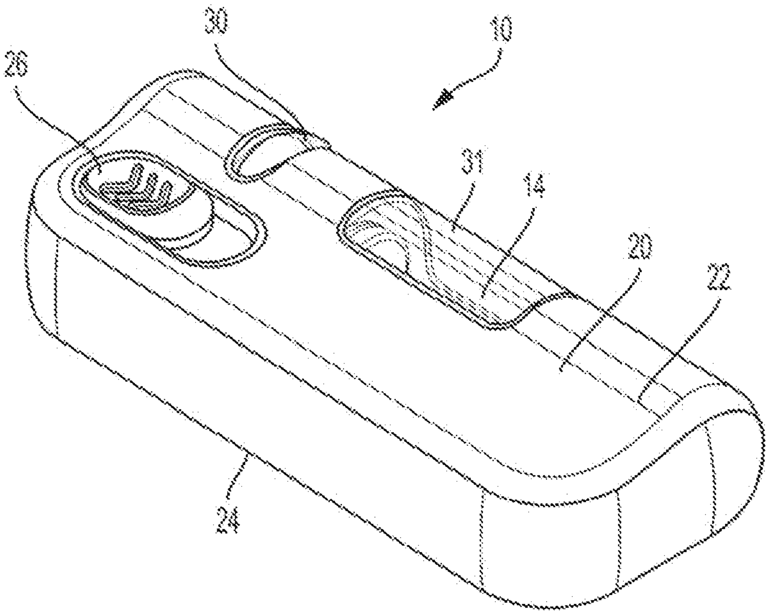
FIG. 1 is a perspective view of a drug delivery system according to one aspect of the present invention.
Figure 2:
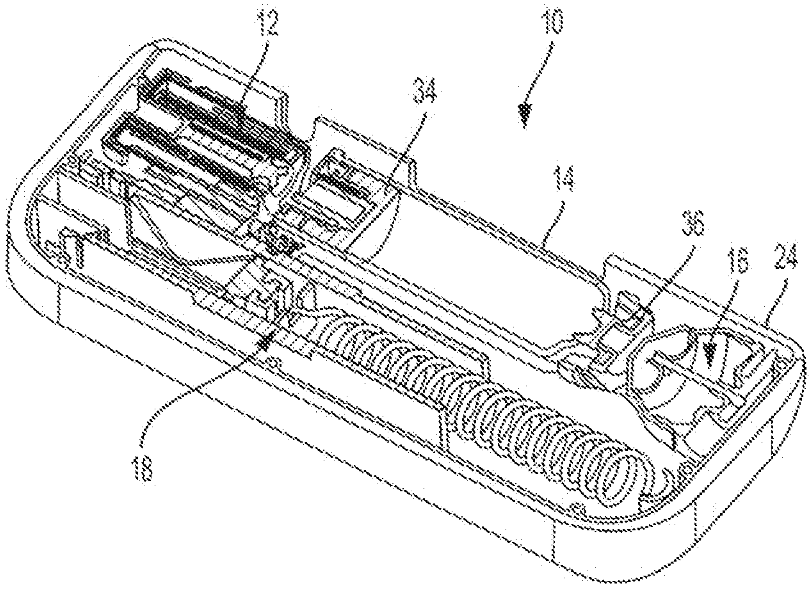
FIG. 2 is a perspective, cross-sectional view of the drug delivery system of FIG. 1 according to one aspect of the present invention.
Figure 3:
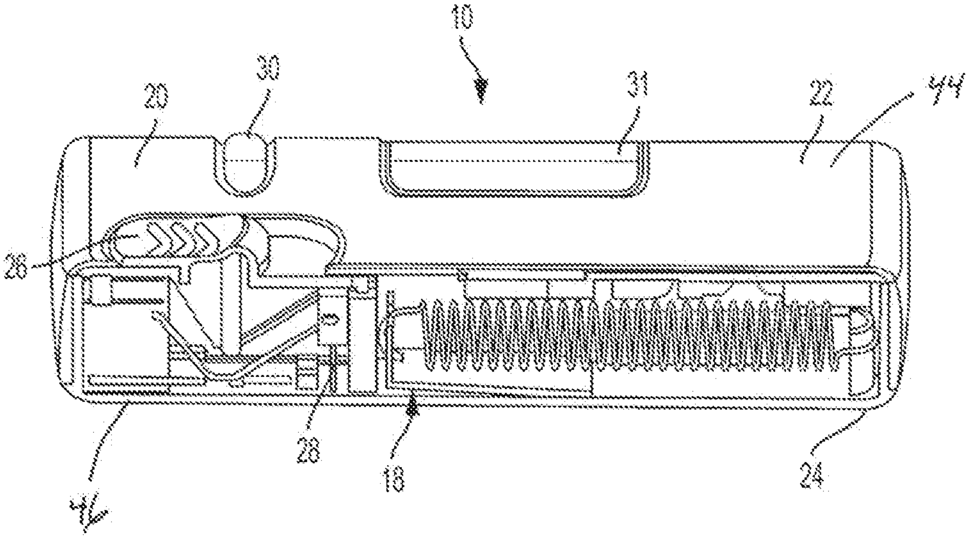
FIG. 3 is a front, cross-sectional view of the drug delivery system of FIG. 1 according to one aspect of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral". "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-15, a drug delivery device 10 according to one aspect of the present disclosure includes a drive assembly 12, a container 14, a valve assembly 16, and a needle actuator assembly 18. The drive assembly 12, the container 14, the valve assembly 16, and the needle actuator assembly 18 are at least partially positioned within a cavity defined by a housing 20. The housing 20 includes a top portion 22 and a bottom portion 24, although other suitable arrangements for the housing 20 may be utilized. In one aspect, the drug delivery device 10 is an injector device configured to be worn or secured to a user and to deliver a predetermined dose of a medicament provided within the container 14 via injection into the user. The device 10 may be utilized to deliver a "bolus injection" where a medicament is delivered within a set time period. The medicament may be delivered over a time period of up to 45 minutes, although other suitable injection amounts and durations may be utilized. A bolus administration or delivery can be carried out with rate controlling or have no specific rate controlling. The device 10 may deliver the medicament at a fixed pressure to the user with the rate being variable. The general operation of the device 10 is described below in reference to FIGS. 1-15.

Referring again to FIGS. 1-15, the device 10 is configured to operate through the engagement of an actuation button 26 by a user, which results in a needle 28 of the needle assembly 18 piercing the skin of a user, the actuation of the drive assembly 12 to place the needle 28 in fluid communication with the container 14 and to expel fluid or medicament from the container 14, and the withdrawal of the needle 28 after injection of the medicament is complete. The general operation of a drug delivery system is shown and described in International Publication Nos. 2013/155153 and 2014/179774, which are hereby incorporated by reference in their entirety. The housing 20 of the device 10 includes an indicator window 30 for viewing an indicator arrangement 32 configured to provide an indication to a user on the status of the device 10 and a container window 31 for viewing the container 14. The indicator window 30 may be a magnifying lens for providing a clear view of the indicator arrangement 32. The indicator arrangement 32 moves along with the needle actuator assembly 18 during use of the device 10 to indicate a pre-use status, use status, and post-use status of the device 10. The indicator arrangement 32 provides visual indicia regarding the status, although other suitable indicia, such as auditory or tactile, may be provided as an alternative or additional indicia.

Figure 4:
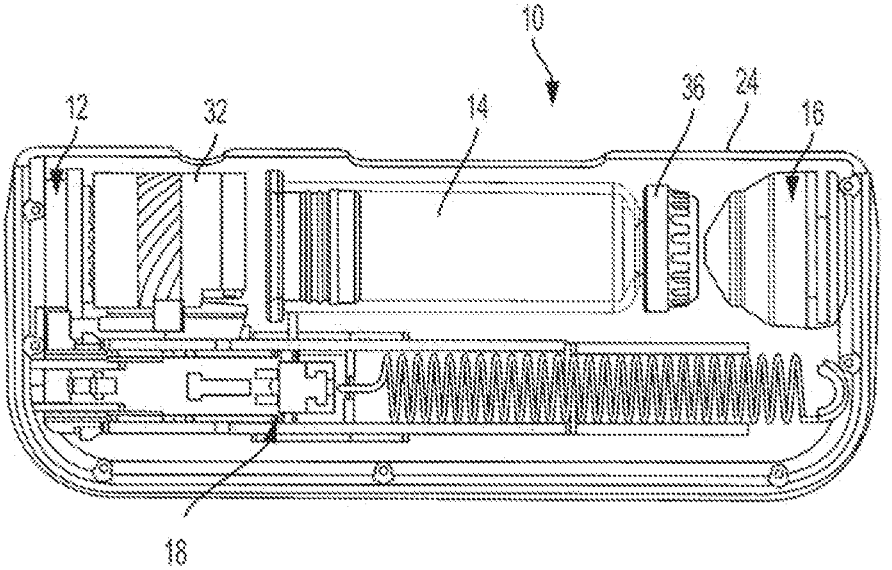
FIG. 4 is a top view of the drug delivery system of FIG. 1 according to one aspect of the present invention, showing a top portion of the housing removed and the drug delivery system in a pre-use position.
Figure 5:
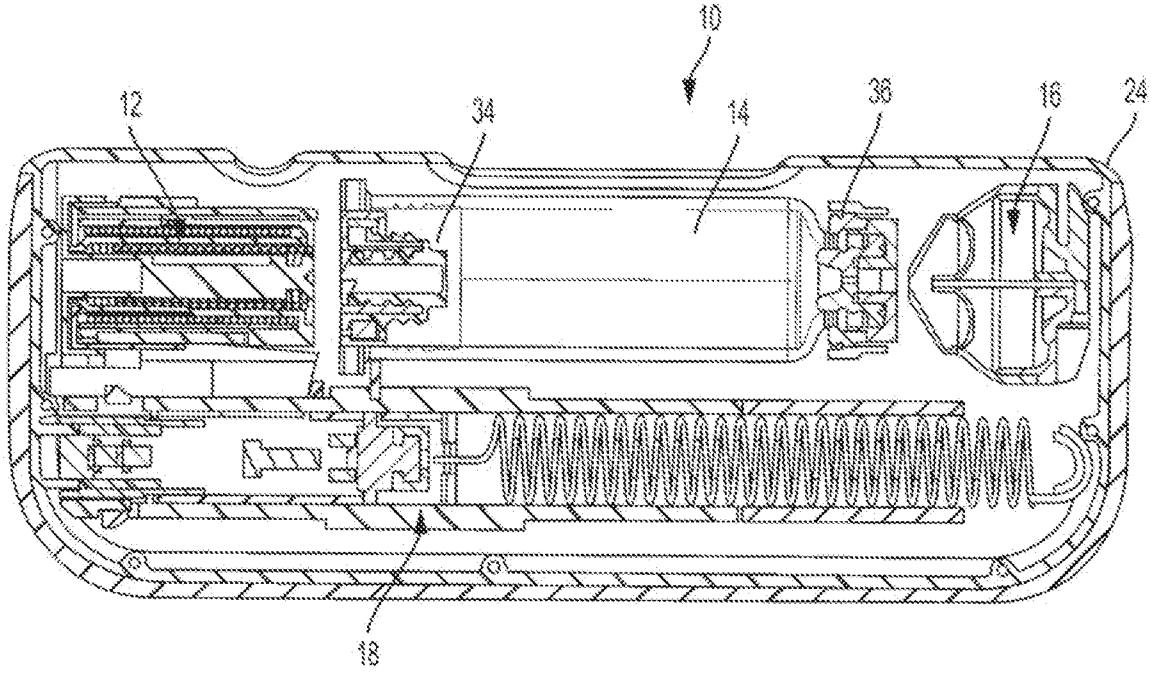
FIG. 5 is a top, cross-sectional view of the drug delivery system of FIG. 1 according to one aspect of the present invention, showing the drug delivery system in a pre-use position.
Figure 6:
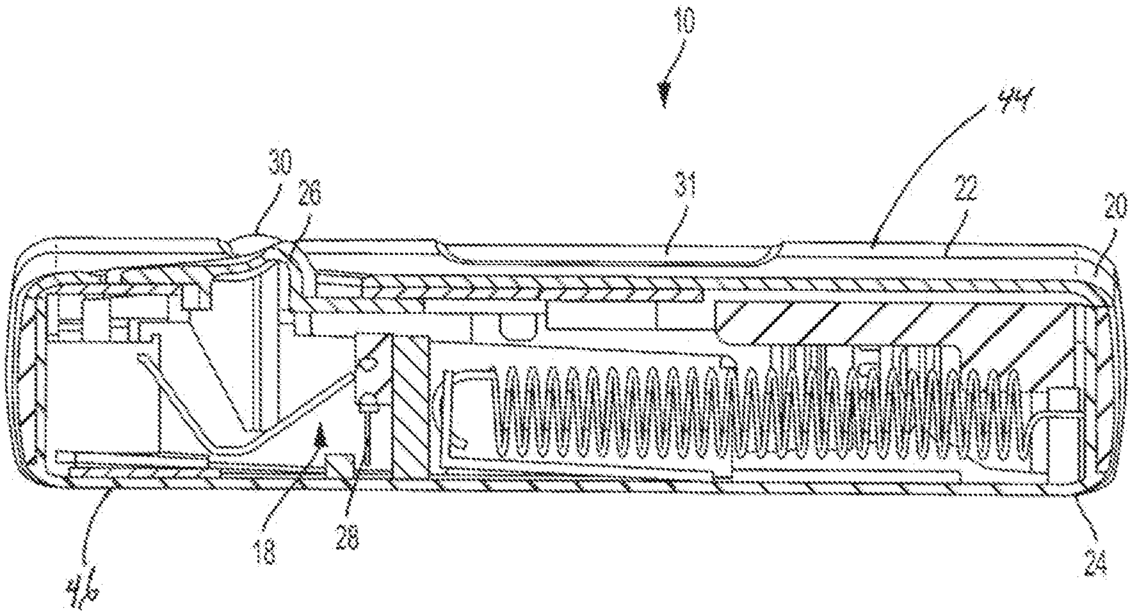
FIG. 6 is a front, cross-sectional view of the drug delivery system of FIG. 1 according to one aspect of the present invention, showing the drug delivery system in a pre-use position.
Figure 7:
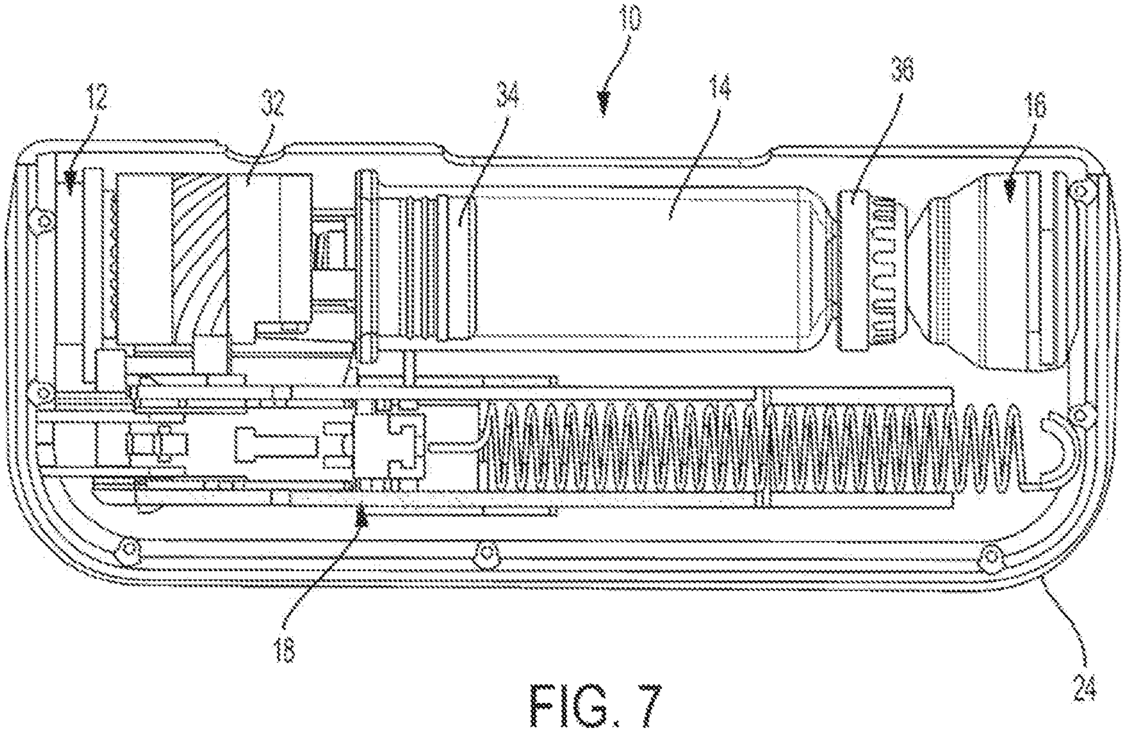
FIG. 7 is a top view of the drug delivery system of FIG. 1 according to one aspect of the present invention, showing a top portion of the housing removed and the drug delivery system in an initial actuation position.
Figure 8:
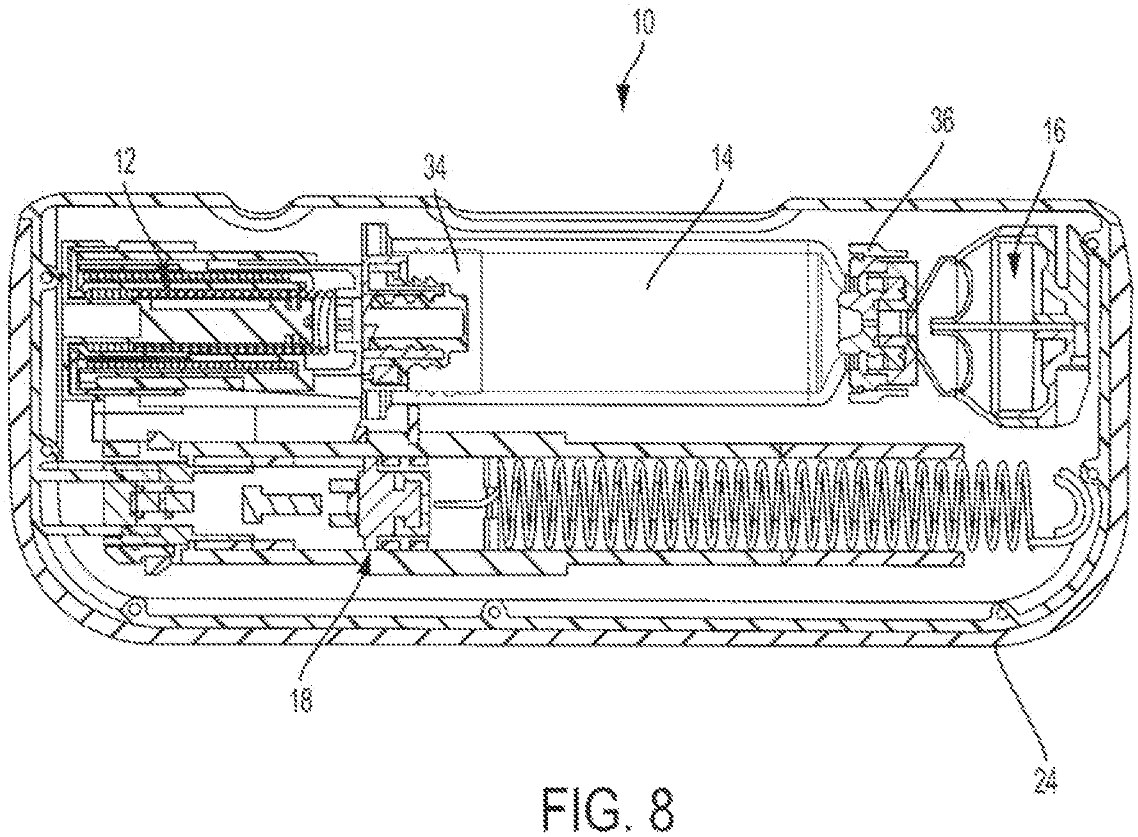
FIG. 8 is a top, cross-sectional view of the drug delivery system of FIG. 1 according to one aspect of the present invention, showing the drug delivery system in an initial actuation position.
Figure 9:
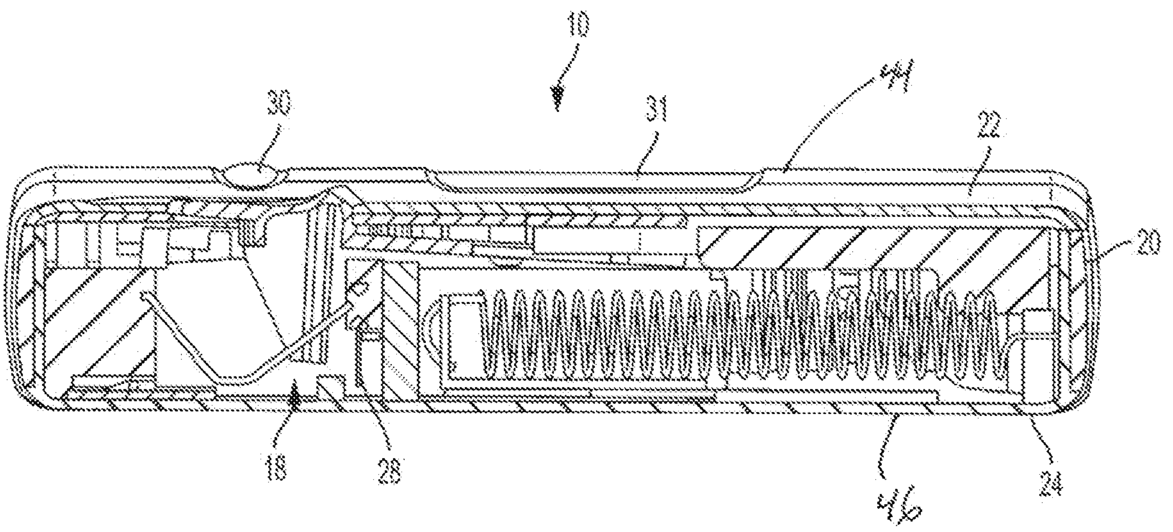
FIG. 9 is a front, cross-sectional view of the drug delivery system of FIG. 1 according to one aspect of the present invention, showing the drug delivery system in an initial actuation position.

Referring to FIGS. 4-6, during a pre-use position of the device 10, the container 14 is spaced from the drive assembly 12 and the valve assembly 16 and the needle 28 is in a retracted position. During the initial actuation of the device 10, as shown in FIGS. 7-9, the drive assembly 12 engages the container 14 to move the container 14 toward the valve assembly 16, which is configured to pierce a closure 36 of the container 14 and place the medicament within the container 14 in fluid communication with the needle 28 via a tube (not shown) or other suitable arrangement. The drive assembly 12 is configured to engage a stopper 34 of the container 14, which will initially move the entire container 14 into engagement with the valve assembly 16 due to the incompressibility of the fluid or medicament within the container 14. More specifically, the drive assembly 12 is configured to engage a spacer 40 received by the stopper 34. The initial actuation of the device 10 is caused by engagement of the actuation button 26 by a user, which releases the needle actuator assembly 18 and the drive assembly 12 as discussed below in more detail. During the initial actuation, the needle 28 is still in the retracted position and about to move to the extended position to inject the user of the device 10.

Figure 10:
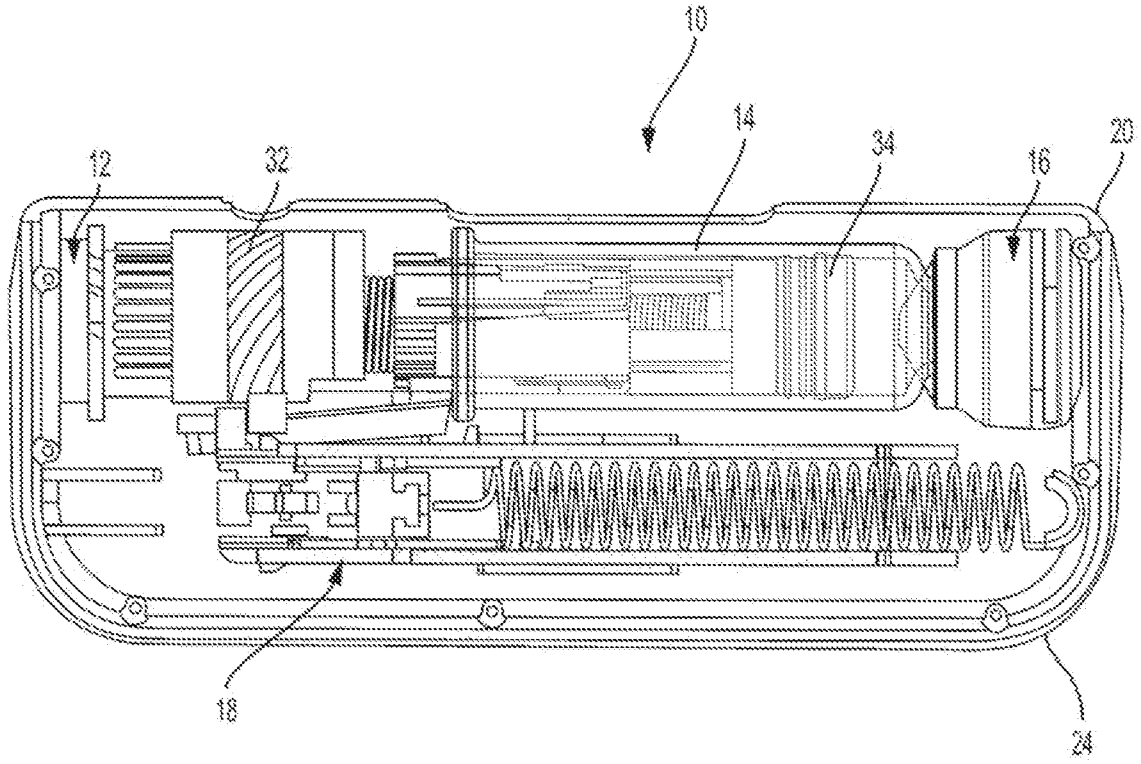
FIG. 10 is a top view of the drug delivery system of FIG. 1 according to one aspect of the present invention, showing a top portion of the housing removed and the drug delivery system in a use position.
Figure 11:
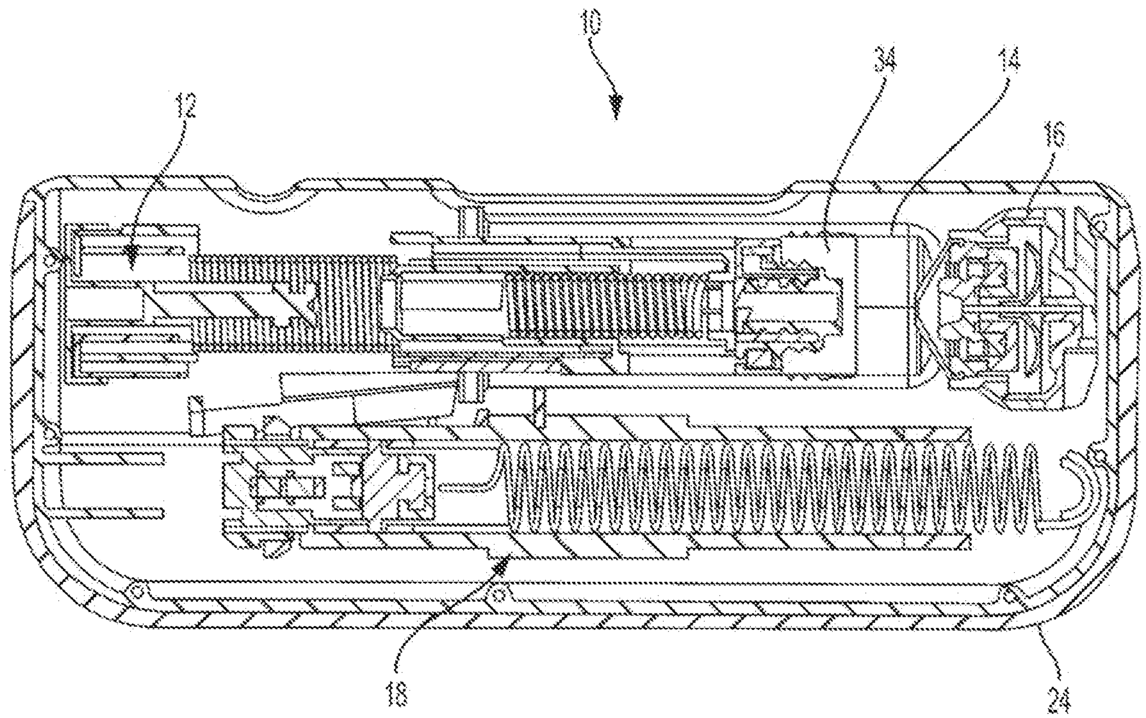
FIG. 11 is a top, cross-sectional view of the drug delivery system of FIG. 1 according to one aspect of the present invention, showing the drug delivery system in a use position.
Figure 12:
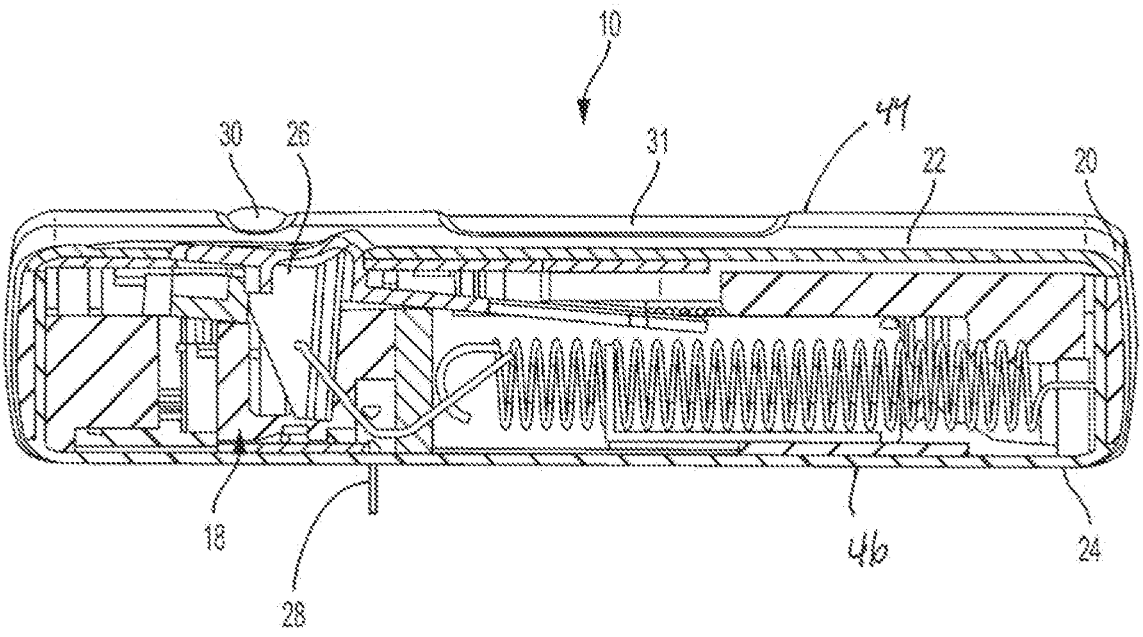
FIG. 12 is a front, cross-sectional view of the drug delivery system of FIG. 1 according to one aspect of the present invention, showing the drug delivery system in a use position.
Figure 13:
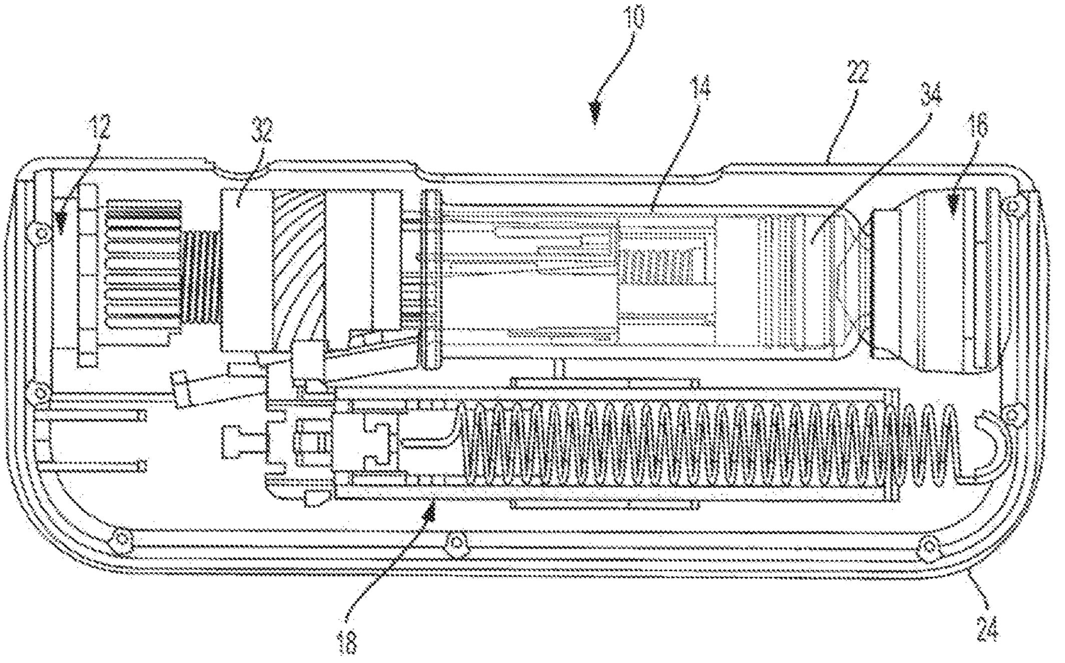
FIG. 13 is a top view of the drug delivery system of FIG. 1 according to one aspect of the present invention, showing a top portion of the housing removed and the drug delivery system in a post-use position.
Figure 14:
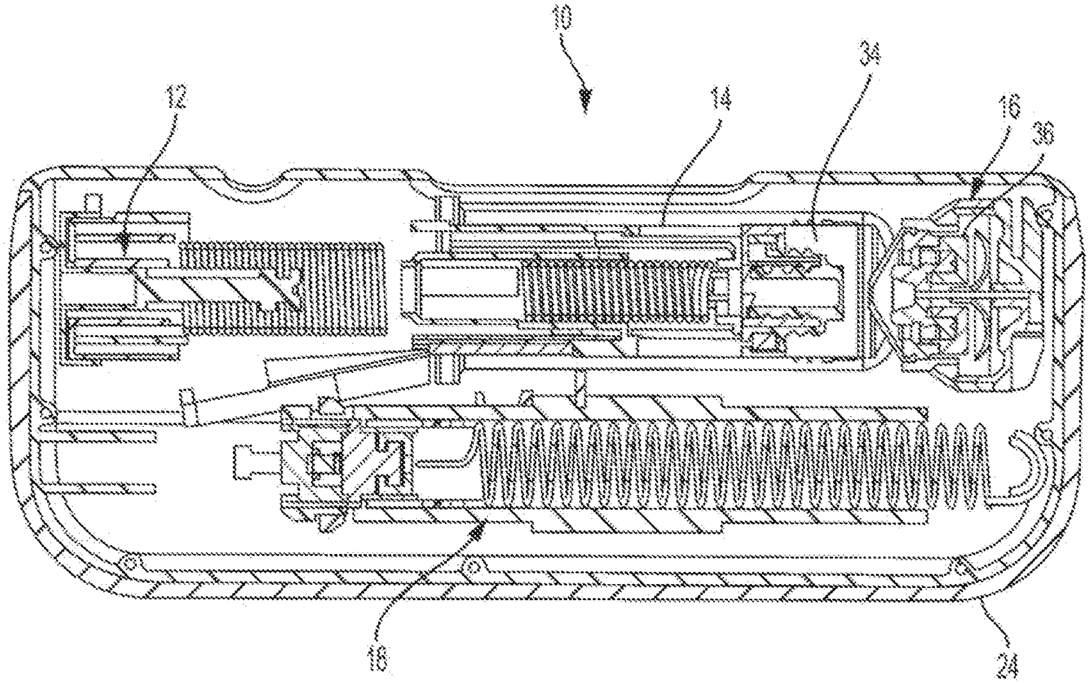
FIG. 14 is a top, cross-sectional view of the drug delivery system of FIG. 1 according to one aspect of the present invention, showing the drug delivery system in a post-use position.
Figure 15:
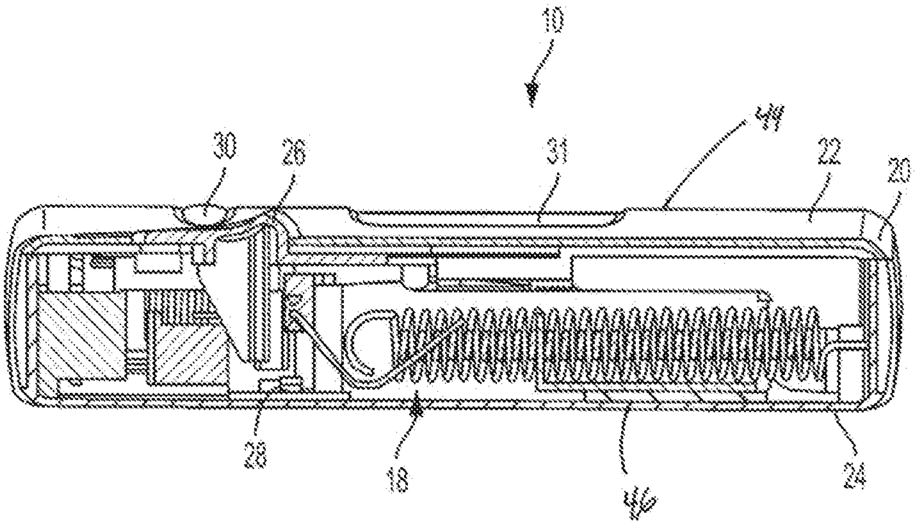
FIG. 15 is a front, cross-sectional view of the drug delivery system of FIG. 1 according to one aspect of the present invention, showing the drug delivery system in a post-use position.

During the use position of the device 10, as shown in FIGS. 10-12, the needle 28 is in the extended position at least partially outside of the housing 20 with the drive assembly 12 moving the stopper 34 within the container 14 to deliver the medicament from the container 14, through the needle 28, and to the user. In the use position, the valve assembly 16 has already pierced a closure 36 of the container 14 to place the container 14 in fluid communication with the needle 28, which also allows the drive assembly 12 to move the stopper 34 relative to the container 14 since fluid is able to be dispensed from the container 14. At the post-use position of the device 10, shown in FIGS. 13-15, the needle 28 is in the retracted position and engaged with a pad 38 to seal the needle 28 and prevent any residual flow of fluid or medicament from the container 14. The container 14 and valve assembly 16 may be the container 14 and valve assembly 16 shown and described in International Publication No. WO 2015/081337, which is hereby incorporated by reference in its entirety.

Figure 19:
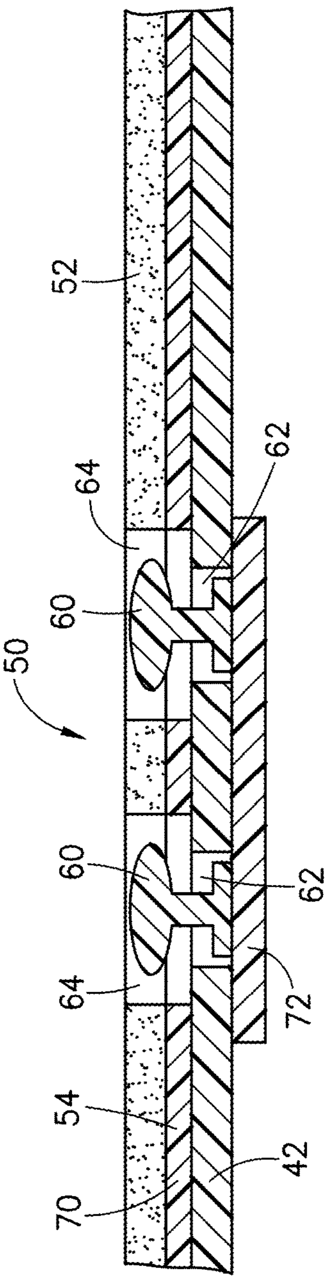
FIG. 19 is a partial cross-sectional view of the adhesive assembly and needle shield of FIG. 16, showing a liner of the adhesive assembly secured to the needle shield.
Figure 20:
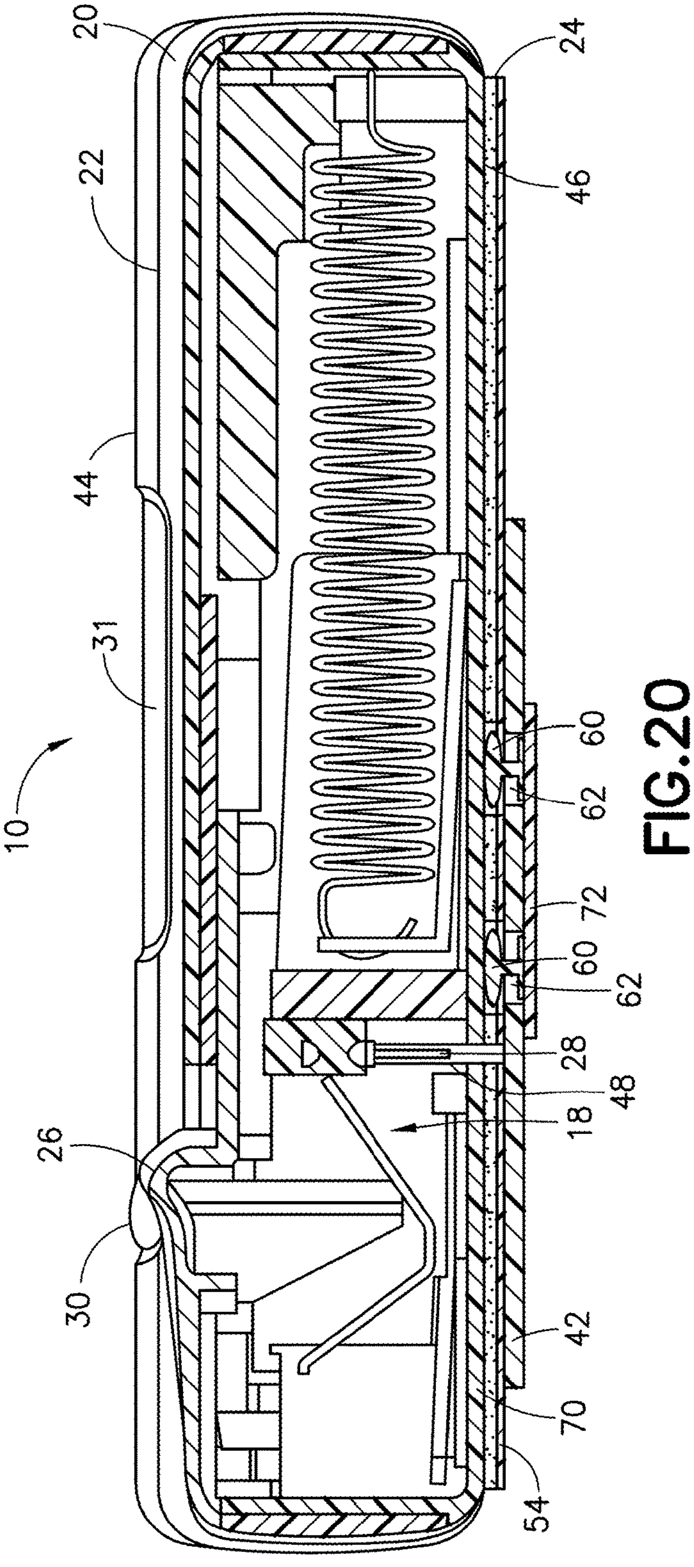
FIG. 20 is a cross-sectional view of the adhesive assembly and needle shield of FIG. 16, showing the adhesive assembly and the needle shield secured to the drug delivery device of FIG. 1.

Referring to FIGS. 16-20, the drug delivery device 10 of FIGS. 1-15 may be provided with a needle shield 42 secured to the housing 20 and receiving a portion of the needle 28. The housing 20 includes a top surface 44 and a bottom surface 46. The needle shield 42 includes a cylindrical portion 48 received within the housing 20 that surrounds at least a portion of the needle 28. The needle shield 42 may be secured to the housing 20 by gripping or engaging a portion of the housing 20 or may be secured to the housing 20 via a friction fit with an opening of the housing 20. The needle shield 42 maintains the sterility of the needle 28 in the pre-use position and may also be configured to prevent accidental actuation of the drug delivery device 10. The drug delivery device 10 may also include an adhesive assembly 50 configured to secure the drug delivery device 10 to a patient to enable the delivery of medicament from the container 14 into the patient subcutaneously and allow removal of the device 10 from the patient after completion of the delivery of the medicament. The adhesive assembly 50 includes an adhesive layer 52 secured to the bottom surface 46 of the housing 20 and a liner 54 secured to the adhesive layer 52. The liner 54 is configured to be removed from the adhesive layer 52 to expose the adhesive layer 52 and to allow the adhesive layer 52 to be affixed to a surface, such as a skin surface of a patient. The liner 54 includes a protrusion(s) 60 and the needle shield 42 defines a liner opening(s) 62, although the liner 54 may include the liner opening(s) 62 and the needle shield 42 may include the protrusion(s) 60. The liner 54 is shown with two protrusions 60 and the needle shield 42 includes two liner openings 62, although one or more protrusions 60 and liner openings 62 may be utilized. As shown in FIG. 19, the protrusion(s) 60 is received by the liner opening(s) 62 to secure the liner 54 to the needle shield 42. The liner 54 is configured to be separated from the adhesive layer 52 upon removal of the needle shield 42 from the housing 20.

Figure 16:
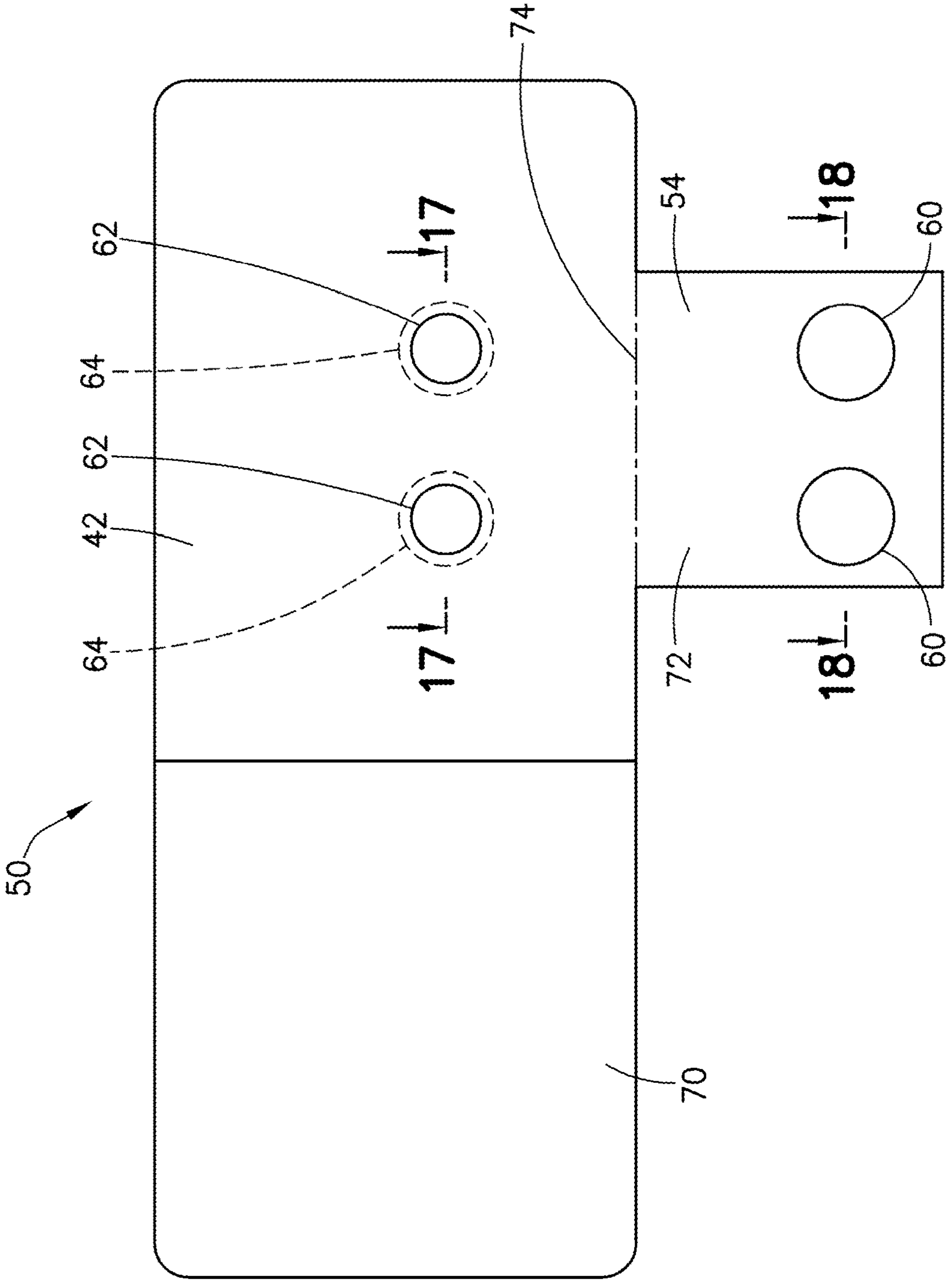
FIG. 16 is a top view of an adhesive assembly and needle shield according to one aspect of the present invention.
Figure 17:
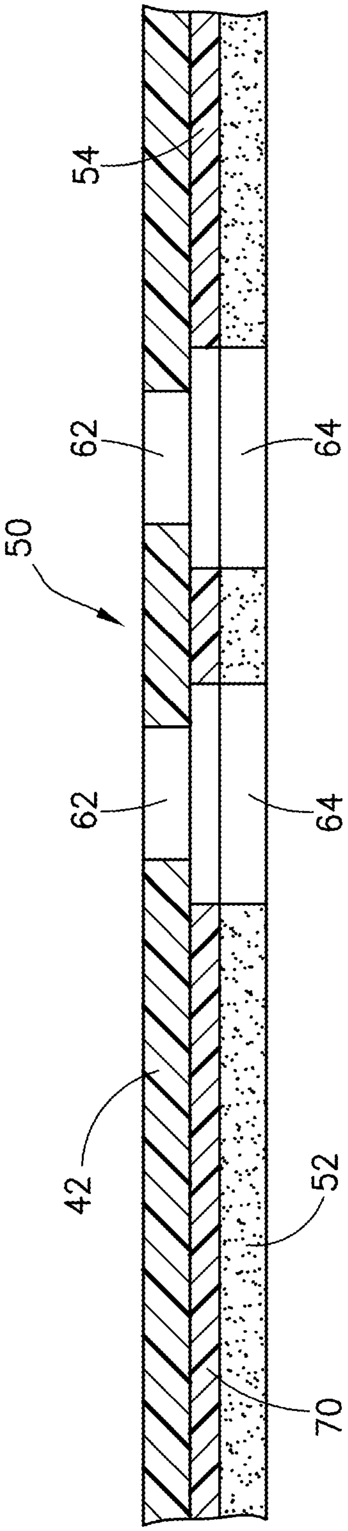
FIG. 17 is a partial cross-sectional view taken along line 17-17 in FIG. 16.
Figure 18:
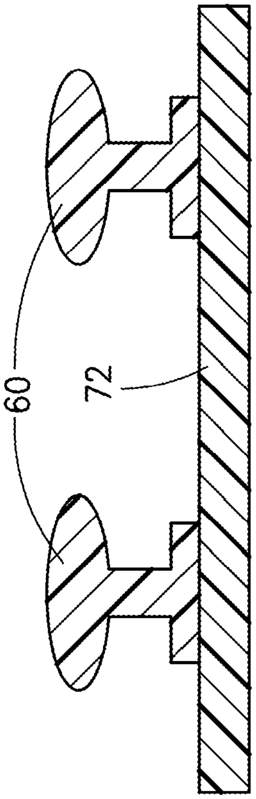
FIG. 18 is a cross-sectional view taken along line 18-18 in FIG. 16.

Referring to FIGS. 16, 17, and 19, the liner 54 and the adhesive layer 52 define a clearance opening 64 that receives a portion of the protrusion(s) 60. The clearance opening 64 provides a space for the protrusion(s) 60 when the protrusion(s) 60 is secured to the needle shield 42.

Referring again to FIGS. 16-20, the liner 54 includes a main body 70 covering at least a portion of the adhesive layer 52 and an extension portion 72 extending from the main body 70. The extension portion 72 of the liner 54 include the protrusion(s) 60. When the liner 54 is secured to the needle shield 42 via the protrusion(s) 60, the needle shield 42 is positioned between the main body 70 of the liner 54 and the extension portion 72 of the liner 54. The adhesive assembly 50, however, may be configured such that the extension portion 72 is positioned between the main body 70 and the needle shield 42 with the protrusion(s) 60 extending from the extension portion 72 toward the needle shield 42 when the needle shield 42 is secured to the liner 54. The main body 70 of the liner 54 entirely covers the adhesive layer 52, although other suitable configurations may be utilized where the main body 70 of the liner 54 only covers a portion of the adhesive layer 52. The protrusion(s) 60 and the liner opening(s) 62 form a snap-fit, which secures the liner 54 to the needle shield 42. The liner 54 includes a folding line 74 separating the main body 70 of the liner 54 from the extension portion 72 of the liner 54, with the extension portion 72 of the liner 54 configured to be folded relative to the main body 70 of the liner 54 about the folding line 74.

When the needle shield 42 is removed from the drug delivery device 10 by grasping the needle shield 42 and moving it away from the bottom surface 46 of the housing 20, the extension portion 72 of the liner 54 will be moved along with the needle shield 42 due to the connection of the extension portion 72 to the needle shield 42 via the protrusion(s) 60 and the liner opening(s) 62. Continued movement of the needle shield 42 and the extension portion 72 of the liner 54 causes the extension portion 72 of the liner 54 to peel the main body 70 of the liner 54 from the adhesive layer 52. The extension portion 72 of the liner 54 is attached at a perimeter of the main body 70 of the liner 54, which helps facilitate the peeling of the liner 54 from the adhesive layer 52, although other suitable arrangements may be utilized.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A drug delivery device comprising:

a housing having a top surface and a bottom surface;

a container received within the housing, the container configured to receive a medicament, the container comprising a stopper configured to move within the container;

a drive assembly configured to move the stopper;

a needle having a retracted position where the needle is positioned within the housing and an extended position where a portion of the needle protrudes from the housing;

a needle shield secured to the housing and receiving a portion of the needle; and an adhesive assembly comprising an adhesive layer secured to the bottom surface of the housing and a liner secured to the adhesive layer, the liner configured to be removed from the adhesive layer, wherein the liner comprises a protrusion and the needle shield comprises a liner opening, wherein the protrusion is received by the liner opening to secure the liner to the needle shield, wherein the liner is configured to be separated from the adhesive layer upon removal of the needle shield from the housing, wherein the liner and the adhesive layer define a clearance opening that receives a portion of the protrusion.

2. The device of claim 1, wherein the liner comprises a main body covering at least a portion of the adhesive layer and an extension portion extending from the main body, wherein the extension portion of the liner comprises the protrusion.

3. The device of claim 2, wherein the needle shield is positioned between the main body of the liner and the extension portion of the liner.

4. The device of claim 2, wherein the main body of the liner entirely covers the adhesive layer.

5. The device of claim 1, wherein the protrusion and the liner opening form a snap-fit.

6. An adhesive assembly for a drug delivery device comprising a housing, a needle having a retracted position where the needle is positioned within the housing and an extended position where a portion of the needle protrudes from the housing, and a needle shield secured to the housing and receiving a portion of the needle, the adhesive assembly comprising:

an adhesive layer configured to be secured to a bottom surface of the housing; and a liner secured to the adhesive layer, the liner configured to be removed from the adhesive layer, the liner comprising a protrusion configured to be received by a liner opening defined by the needle shield, wherein the liner is configured to be separated from the adhesive layer upon removal of the needle shield from the housing, wherein the liner and the adhesive layer define a clearance opening that receives a portion of the protrusion.

7. The assembly of claim 6, wherein the liner comprises a main body covering at least a portion of the adhesive layer and an extension portion extending from the main body, the protrusion positioned on the extension portion of the liner.

8. The assembly of claim 7, wherein the liner comprises a folding line separating the main body of the liner from the extension portion of the liner, the extension portion of the liner configured to be folded relative to the main body of the liner about the folding line.

9. The assembly of claim 7, wherein the main body of the liner entirely covers the adhesive layer.

10. The assembly of claim 6, wherein the protrusion of the liner is configured to be snap-fit to the needle shield.

* * * * *